(12) United States Patent
Koike et al.

(10) Patent No.: US 8,263,121 B2
(45) Date of Patent: Sep. 11, 2012

(54) SOLID PHARMACEUTICAL PREPARATION

(75) Inventors: Masahiko Koike, Osaka (JP); Hiroyoshi Koyama, Osaka (JP); Naoru Hamaguchi, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 779 days.

(21) Appl. No.: 11/578,450

(22) PCT Filed: Apr. 13, 2005

(86) PCT No.: PCT/JP2005/007484
§ 371 (c)(1),
(2), (4) Date: Oct. 13, 2006

(87) PCT Pub. No.: WO2005/099760
PCT Pub. Date: Oct. 27, 2005

(65) Prior Publication Data
US 2007/0166376 A1 Jul. 19, 2007

(30) Foreign Application Priority Data
Apr. 14, 2004 (JP) ................................. 2004-118907

(51) Int. Cl.
*A61K 31/4439* (2006.01)
*A61K 31/155* (2006.01)
*A61K 9/201* (2006.01)

(52) U.S. Cl. .......................... 424/464; 514/342; 514/635

(58) Field of Classification Search .................... None
See application file for complete search history.

(56) References Cited

U.S. PATENT DOCUMENTS

| 5,609,882 | A | * | 3/1997 | Aoki et al. | 424/451 |
| 6,403,121 | B1 | | 6/2002 | Adjei et al. | |
| 6,475,521 | B1 | * | 11/2002 | Timmins et al. | 424/469 |
| 6,524,621 | B2 | | 2/2003 | Adjei et al. | |
| 2002/0004515 | A1 | | 1/2002 | Smith | |
| 2002/0012700 | A1 | * | 1/2002 | Johnson et al. | 424/464 |
| 2006/0286168 | A1 | | 12/2006 | Koike et al. | |

FOREIGN PATENT DOCUMENTS

| EP | 0 220 805 | | 5/1987 |
| JP | 2000-336027 | | 12/2000 |
| JP | 2003-144528 | | 5/2003 |
| WO | WO-98/57634 | | 12/1998 |
| WO | WO-99/47128 | | 9/1999 |
| WO | WO 00/28989 | * | 11/1999 |
| WO | PCT/EP99/08704 | * | 5/2000 |
| WO | WO-00/28989 | | 5/2000 |
| WO | WO-01/35940 A2 | | 5/2001 |
| WO | WO-01/35941 A2 | | 5/2001 |
| WO | WO-01/49292 A1 | | 7/2001 |
| WO | WO-01/82875 A2 | | 11/2001 |
| WO | PCT/US03/08945 | * | 2/2003 |
| WO | WO 03/080056 A2 | * | 10/2003 |
| WO | WO-2004/006921 A1 | | 1/2004 |
| WO | WO-2004/006921 A1 | | 1/2004 |
| WO | WO-2004/030700 A1 | | 4/2004 |
| WO | WO-2004/067001 A1 | | 8/2004 |

OTHER PUBLICATIONS

Ishikawa et al., Chemical Pharmaceutical Bulletin, 49(2) 134-139 (2001).*
Tatsuya et al., "Preparation of Rapidly Disintegrating Tablet Using New Types of Microcrystalline Cellulose (PH-M Series) and Low Substituted-Hydroxypropylcellulose or Spherical Sugar Granules by Direct Compression Method", *Chemical and Pharmaceutical Bulletin*, vol. 49, No. 2, pp. 134-139 (Feb. 2001).
Fiedler et al., "Fiedler Lexikon der Hilfsstoffe", *Editio Cantor Verlag*, pp. 275-279(2002).
Gennaro et al., "Remington: The Science and Practice of Pharmacy", *Mack Publishing Company*, Easton, PA, pp. 1615-1620 (1995).

* cited by examiner

*Primary Examiner* — Ernst Arnold
*Assistant Examiner* — Hong Yu
(74) *Attorney, Agent, or Firm* — Edwards Wildman Palmer LLP; David G. Conlin; Mark D. Russett

(57) ABSTRACT

The present invention provides a solid preparation containing an insulin sensitizer and an active ingredient (except insulin sensitizers), which shows in vivo dissolution behavior of an insulin sensitizer, which is similar to the dissolution behavior of an insulin sensitizer from "a solid preparation containing an insulin sensitizer alone as an active ingredient".

The present invention provides a solid preparation containing (1) a layer containing an insulin sensitizer, and (2) a layer containing (a) an active ingredient (except insulin sensitizers), (b) microcrystalline cellulose having a mean particle size of 5-25 μm, (c) microcrystalline cellulose having a mean particle size of 30-100 μm and (d) polyvinylpyrrolidone K-90.

9 Claims, No Drawings

SOLID PHARMACEUTICAL PREPARATION

TECHNICAL FIELD

The present invention relates to a solid preparation comprising an insulin sensitizer and an active ingredient (except insulin sensitizers), which is useful as a therapeutic drug for diabetes and the like.

BACKGROUND ART

There are the following reports on preparations containing an insulin sensitizer such as a thiazolidinedione and the like and an active ingredient (except insulin sensitizers).
1) A pharmaceutical composition containing an insulin sensitizer, a biguanide antihyperglycaemic agent and a pharmaceutically acceptable carrier (WO98/57634, US2002/0004515A).
2) A pharmaceutical composition containing an insulin sensitizer, other antidiabetic drug and a pharmaceutically acceptable carrier therefor, which is controlled to modify release of at least one of the insulin sensitizer and other antidiabetic drug (WO00/28989).
3) A pharmaceutical composition containing a thiazolidinedione, metformin hydrochloride and a pharmaceutically acceptable carrier, wherein the thiazolidinedione is formulated upon the surface of metformin hydrochloride (WO01/35940).
4) A pharmaceutical composition containing a thiazolidinedione, metformin hydrochloride and a pharmaceutically acceptable carrier, wherein the thiazolidinedione and metformin hydrochloride are respectively dispersed in pharmaceutically acceptable carriers of their own (WO01/35941).
5) A core formulation comprising (a) a first layer containing pioglitazone hydrochloride or a pharmaceutically acceptable salt thereof as an active ingredient, and (b) a core containing a biguanide as an active ingredient, wherein at least a portion of the core is enclosed by said first layer (WO01/82875).
6) (a) a core formulation comprising a first layer containing pioglitazone hydrochloride or a pharmaceutically acceptable salt thereof as an active ingredient, (b) a core containing a biguanide as an active ingredient, wherein at least a portion of the core is enclosed by said first layer, and (c) a modulating polymer comprising polysaccharides relating to at least one of the aforementioned active ingredients (U.S. Pat. No. 6,403,121).
7) (a) a core formulation comprising a first layer containing pioglitazone hydrochloride or a pharmaceutically acceptable salt thereof as an active ingredient, (b) a core containing a biguanide as an active ingredient, wherein at least a portion of the core is enclosed by said first layer, and (c) silicate comprising polysaccharides relating to at least one of the aforementioned active ingredients (U.S. Pat. No. 6,524,621).
8) a production method of a coated preparation, which comprises coating with a dispersion of pioglitazone hydrochloride in an organic solvent, which contains a coating base soluble in organic solvents (WO2004/006921).

DISCLOSURE OF THE INVENTION

In a solid preparation comprising an insulin sensitizer and an active ingredient (except insulin sensitizers), these active ingredients preferably show bioequivalence to two kinds of solid preparations independently containing these active ingredients.

The present inventors have studied in vivo dissolution property of an insulin sensitizer and an active ingredient (except insulin sensitizers) from a solid preparation containing these ingredients, and first found a problem in that the dissolution of the insulin sensitizer from the solid preparation is influenced by the aforementioned active ingredient (except insulin sensitizers), and tends to be slow as compared to the dissolution of the insulin sensitizer from "a solid preparation containing an insulin sensitizer alone as an active ingredient".

The present inventors conducted intensive studies in an attempt to solve the above-mentioned problems, and found that a solid preparation comprising an insulin sensitizer and an active ingredient (except insulin sensitizers) in separate layers, and two kinds of microcrystalline cellulose having a different mean particle size and polyvinylpyrrolidone K-90 in the layer containing the active ingredient (except insulin sensitizers) shows an in vivo dissolution behavior of the insulin sensitizer, which is similar to that from "a solid preparation containing an insulin sensitizer alone as an active ingredient".

Accordingly, the present invention relates to
1) a solid preparation comprising (1) a layer containing an insulin sensitizer and (2) a layer containing (a) an active ingredient (except insulin sensitizers), (b) microcrystalline cellulose having a mean particle size of 5-25 μm, (c) microcrystalline cellulose having a mean particle size of 30-100 μm and (d) polyvinylpyrrolidone K-90 (hereinafter sometimes to be abbreviated as the solid preparation of the present invention);
2) the solid preparation of the aforementioned 1), wherein the insulin sensitizer is pioglitazone hydrochloride;
3) the solid preparation of the aforementioned 1), wherein the active ingredient (except insulin sensitizers) is biguanide;
4) the solid preparation of the aforementioned 3), wherein the biguanide is metformin hydrochloride;
5) the solid preparation of the aforementioned 1), wherein the insulin sensitizer has a median size of 1 to 70 μm;
6) the solid preparation of the aforementioned 3), wherein the biguanide has a median size of 10 to 100 μm;
7) the solid preparation of the aforementioned 1), wherein the polyvinylpyrrolidone K-90 content is 0.1-20 parts by weight per 100 parts by weight of the solid preparation;
8) the solid preparation of the aforementioned 1), which is a tablet;
9) the solid preparation of the aforementioned 1), which is a multiplelayer tablet;
10) a production method of the solid preparation of the aforementioned 1), which comprises stacking (1) a layer containing an insulin sensitizer, and (2) a layer containing (a) an active ingredient (except insulin sensitizers), (b) microcrystalline cellulose having a mean particle size of 5-25 μm, (c) microcrystalline cellulose having a mean particle size of 30-100 μm and (d) polyvinylpyrrolidone K-90 in layers and compression-shaping them;
11) the production method of the aforementioned 10), wherein the compression-shaping is tableting;
12) a solid preparation comprising (1) metformin or a salt thereof, (2) microcrystalline cellulose having a mean particle size of 5-25 μm and (3) microcrystalline cellulose having a mean particle size of 30-100 μm, wherein release of the metformin or a salt thereof is controlled; and the like.

The solid preparation of the present invention is useful as a therapeutic drug for diabetes and the like, and shows bioequivalence to two kinds of solid preparations independently containing an insulin sensitizer and an active ingredient (except insulin sensitizers).

In particular, the solid preparation of the present invention shows in vivo dissolution behavior of an insulin sensitizer, which is similar to that of an insulin sensitizer from "a solid preparation containing an insulin sensitizer alone as an active ingredient".

BEST MODE FOR EMBODYING THE INVENTION

The insulin sensitizer to be used in the present invention may be any pharmaceutical agent as long as it restores damaged insulin receptor function and improves insulin resistance. As specific examples of the insulin sensitizer, the following compounds and salts thereof can be mentioned:
Pioglitazone; rosiglitazone; netoglitazone; 5-(2,4-dioxothiazolidin-5-ylmethyl)-2-methoxy-N-[4-(trifluoromethyl) benzyl]benzamide (KRP-297); Reglixane; FK-614; Tesaglitazar; Ragaglitazar (NN-622); Balaglitazone; Muraglitazar (BMS-298585); ONO-5816; Rivoglitazone (CS-011); BM-13-1258; LM-4156; MBX-102; Naveglitazar (LY-519818); MX-6054; LY-510929; (E)-4-[4-(5-methyl-2-phenyl-4-oxazolylmethoxy)benzyloxyimino]-4-phenylbutyric acid; T-131; THR-0921.

As the salt of the above-mentioned compound, pharmacologically acceptable salts such as salts with inorganic base, salts with organic base, salts with inorganic acid, salts with organic acid, salts with basic or acidic amino acid and the like can be mentioned.

As preferable examples of the salts with inorganic base, salts with alkali metals (e.g. sodium, potassium and the like), alkaline earth metals (e.g. calcium, magnesium and the like), aluminum, ammonium and the like can be mentioned.

As preferable examples of the salts with organic base, salts with trimethylamine, triethylamine, pyridine, picoline, ethanolamine, diethanolamine, triethanolamine, dicyclohexylamine, N,N-dibenzylethylenediamine and the like can be mentioned.

As preferable examples of the salts with inorganic acid, salts with hydrochloric acid, hydrobromic acid, nitric acid, sulfuric acid, phosphoric acid and the like can be mentioned.

As preferable examples of the salts with organic acid, salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like can be mentioned.

As preferable examples of the salts with basic amino acid, salts with arginine, lysine, ornithine and the like can be mentioned, and as preferable examples of the salts with acidic amino acid, for example, salts with aspartic acid, glutamic acid and the like can be mentioned.

The insulin sensitizer is preferably a thiazolidinedione compound, more preferably pioglitazone hydrochloride, rosiglitazone maleate and the like, and particularly preferably pioglitazone hydrochloride.

In the present invention, two or more kinds of the insulin sensitizers may be used in combination at an appropriate ratio.

The median size of the insulin sensitizer is preferably 1-100 µm, more preferably 1-70 µm. Particularly, when the insulin sensitizer is pioglitazone hydrochloride, the median size of pioglitazone hydrochloride-is preferably 1-50 µm, more preferably 2-30 µm. Particularly, by the use of pioglitazone hydrochloride having a median size of 2 to 25 µm, a solid preparation superior in dissolution property of pioglitazone hydrochloride can be obtained.

The above-mentioned preferable median size is applied to an insulin sensitizer used as a starting material (including a pulverized product obtained by pulverizing, a mixed pulverized product obtained by pulverizing together with an excipient, and the like during the production process of a solid preparation) for producing the solid preparation of the present invention. In other words, the median size of an insulin sensitizer may have changed due to the coagulation of insulin sensitizer and the like, during the production process of the solid preparation of the present invention, or during the process of preserving the solid preparation after production.

In the present specification, by the median size is meant a particle size that divides crude particles from fine granules at 50% each in weight distribution. The median size can be measured using, for example, a known measurement device such as a laser diffraction particle distribution apparatus (e.g., HELOS&RODOS (trade name, manufactured by SYMPATEC GmbH) SALD-2000A (trade name) (SHIMADZU CORPORATION)) and the like.

When the laser diffraction particle distribution apparatus is HELOS&RODOS (trade name) (manufactured by SYMPATEC GmbH), for example, the median size can be measured by a dry method under the conditions of focal length of a lens: 100 mm or 200 mm and pressure of pressurized air: 2.0 bar.

As the insulin sensitizer having a desired median size mentioned above, for example, a commercially available product can be used. In addition, the insulin sensitizer having a desired median size can be also produced by pulverization of an insulin sensitizer having a large median size together with an excipient such as lactose, microcrystalline cellulose and the like as necessary. Here, the pulverization is performed according to a known method using, for example, a cutter mill, a hammer mill, a jet mill and the like.

When an insulin sensitizer is to be pulverized with an excipient, for example, after pulverization, the insulin sensitizer and the excipient are separated utilizing the difference in the solubility (solubility in a particular solvent) between them, and the median size of the obtained insulin sensitizer may be measured.

For example, when a slightly water-soluble compound (e.g., pioglitazone hydrochloride) is used as an insulin sensitizer and a water-soluble substance (e.g., lactose) is used as an excipient, they are pulverized, the water-soluble substance alone is removed from the whole pulverized product by dissolving the water-soluble substance alone in water, and the median size of the aforementioned slightly water-soluble compound (e.g., pioglitazone hydrochloride) alone can be measured.

On the other hand, when a water-insoluble substance such as microcrystalline cellulose and the like is used as an excipient, the water-insoluble substance and the insulin sensitizer are pulverized, the median size of the whole pulverized product and the median size of the water-insoluble substance are respectively measured, the latter median size is subtracted from the former median size, whereby the median size of the aforementioned insulin sensitizer alone can be measured. In this case, the median size of the water-insoluble substance can be measured by removing the insulin sensitizer alone from the whole pulverized product by dissolving the insulin sensitizer alone in a solvent (e.g., ethanol) that dissolves only the insulin sensitizer.

In particular, when a solid preparation is produced using an insulin sensitizer having a weak binding force and a comparatively large median size, use of a large amount of additives such as a binder and the like needs to be designed to achieve sufficient preparation hardness. However, by making the median size of an insulin sensitizer smaller, a large amount of additives such as a binder and the like becomes unnecessary, which makes it possible to increase the drug content of a solid preparation.

As for the insulin sensitizer having a desired median size mentioned above, the dispersibility thereof is preferably such that "particles of not more than 0.1 μm are contained at not more than 10% of the total amount, and particles of not less than 1000 μm are contained at not more than 10% of the total amount".

The content of the insulin sensitizer in the solid preparation of the present invention is, for example, 0.01-100 parts by weight, preferably 1-99 parts by weight, relative to 100 parts by weight of the solid preparation.

In particular, when the insulin sensitizer is pioglitazone hydrochloride, the content of pioglitazone hydrochloride in the solid preparation of the present invention is preferably 0.01-15 parts by weight, more preferably 0.5-10 parts by weight, relative to 100 parts by weight of the solid preparation.

As the active ingredient (except insulin sensitizers) to be used in the present invention, for example, therapeutic agents for diabetes, therapeutic agents for diabetic complications, therapeutic agents for hyperlipidemia, antihypertensive agents, antiobesity agents, diuretics, antithrombotic agents and the like can be mentioned. These active ingredients may be a low-molecular-weight compound, a high-molecular-weight protein, polypeptide or antibody, a vaccine and the like. The active ingredient may be used by mixing two or more kinds of ingredients at an appropriate ratio.

Examples of the therapeutic agents for diabetes include insulin preparations (e.g., animal insulin preparations extracted from the pancreas of bovine, swine; human insulin preparations synthesized by genetic engineering techniques using *Escherichia coli* or yeast; zinc insulin; protamine zinc insulin; fragments or derivatives of insulin (e.g., INS-1)), α-glucosidase inhibitors (e.g., voglibose, acarbose, miglitol, emiglitate), biguanide (e.g., phenformin, metformin, buformin, or a salt thereof (e.g., hydrochloride, fumarate, succinate)), insulin secretagogues [sulfonylureas (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof], GLP-1 receptor agonist [e.g., GLP-1, GLP-1MR agent, NN-2211, exendin-4, BIM-51077, Aib(8,35)hGLP-1(7,37)NH$_2$, CJC-1131], dipeptidylpeptidase IV inhibitors (e.g., NVP-DPP-278, PT-100, NVP-DDP-728, LAF237, P32/98, P93/01, MK-0431, BMS-477118, TS-021), β3 agonists (e.g., CL-316243, SR-58611-A, UL-TG-307, SB-226552, AJ-9677, BMS-196085, AZ-40140), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists) and SGLUT (sodium-glucose cotransporter) inhibitors (e.g., T-1095), 11β-hydroxysteroid dehydrogenase inhibitors (e.g., BVT-3498), adiponectin or agonist thereof, IKK inhibitors(e.g., AS-2868), leptin resistance improver, somatostatin receptor agonists(e.g., compounds described in WO01/25228, WO03/42204, WO98/44921, WO98/45285, WO99/22735), glucokinase activators (e.g., Ro-28-1675).

Examples of the therapeutic agents for diabetic complications include aldose reductase inhibitors (e.g., tolrestat, epalrestat, zenarestat, zopolrestat, minalrestat, fidarestat (SNK-860), CT-112), neurotrophic factors (e.g., NGF, NT-3, BDNF), neurotrophin production-secretion promoters [e.g., neurotrophin production-secretion promoters described in WO01/14372 (e.g., 4-(4-chlorophenyl)-2-(2-methyl-1-imidazolyl)-5-(3-(2-methylphenoxy)propyl)oxazole)], PKC inhibitors (e.g., ruboxistaurin mesylate; LY-333531), AGE inhibitors (e.g., ALT946, pimagedine, pyratoxanthine, N-phenacylthiazolium bromide (ALT766), EXO-226), active oxygen scavengers (e.g., thioctic acid) and cerebral vasodilators (e.g., tiapride, mexiletine), somatostatin receptor agonists(e.g., BIM23190), apoptosis signal regulating kinase-1 (ASK-1)inhibitors.

Examples of the therapeutic agents for hyperlipidemia include HMG-CoA reductase inhibitors (e.g., pravastatin, simvastatin, lovastatin, atorvastatin, fluvastatin, lipantil, cerivastatin, itavastatin, (pitavastatin), rosuvastatin or their salts (e.g., sodium salts, calcium salts)), fibrate compounds (e.g., bezafibrate, beclofibrate, binifibrate, ciprofibrate, clinofibrate, clofibrate, clofibric acid, etofibrate, fenofibrate, gemfibrozil, nicofibrate, pirifibrate, ronifibrate, simfibrate, theofibrate), squalene synthase inhibitors (e.g., compounds described in WO97/10224 (e.g., 1-[[(3R, 5S)-1-(3-acetoxy-2,2-dimethylpropyl)-7-chloro-5-(2,3-dimethoxyphenyl)-2-oxo-1,2,3,5-tetrahydro-4,1-benzooxazepin-3-yl]acetyl]piperidine-4-acetic acid), ACAT inhibitors (e.g., Avasimibe, Eflucimibe), anion exchange resins (e.g., colestyramine), probucol, nicotinic acid drugs (e.g., nicomol, niceritrol), ethyl icosapentate, plant sterols (e.g., soysterol, γ-oryzanol).

Examples of the antihypertensive agents include angiotensin converting enzyme inhibitors (e.g., captopril, enalapril, delapril), angiotensin II receptor antagonists (e.g., candesartan cilexetil, losartan, eprosartan, valsartan, telmisartan, irbesartan, tasosartan), calcium antagonists (e.g., manidipine, nifedipine, nicardipine, amlodipine, efonidipine), potassium channel openers (e.g., levcromakalim, L-27152, AL 0671, NIP-121) and clonidine.

Examples of the antiobesity agents include antiobesity agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonists (e.g., CP-422935); cannabinoid receptor antagonists (e.g., SR-141716, SR-147778); ghrelin antagonist), 11β-hydroxysteroid dehydrogenase inhibitors (e.g., BVT-3498), pancreatic lipase inhibitors (e.g., orlistat, ATL-962), β3 agonists (e.g., CL-316243, SR-58611-A, UL-TG-307, SB-226552, AJ-9677, BMS-196085, AZ-40140), peptidic anorexiants (e.g., leptin, CNTF (Ciliary Neurotropic Factor)), cholecystokinin agonists (e.g., lintitript, FPL-15849), feeding deterrents (e.g., P-57).

Examples of the diuretics include xanthine derivatives (e.g., sodium salicylate and theobromine, calcium salicylate and theobromine), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlortalidone, mefruside, indapamide), azosemide, isosorbide, etacrynic acid, piretanide, bumetanide, furosemide.

Examples of the antithrombotic agents include heparin (e.g., heparin sodium, heparin calcium, dalteparin sodium), warfarin (e.g., warfarin potassium), anti-thrombin drugs (e.g., aragatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride).

The active ingredient (except insulin sensitizers) to be used in the present invention is preferably a therapeutic agent for diabetes, more preferably a biguanide and a sulfonylurea, particularly preferably metformin or a salt thereof (preferably metformin hydrochloride).

The median size of the active ingredient (except insulin sensitizers) is preferably 0.5 to 1000 μm, more preferably 1 to 200 μm. Particularly, when the active ingredient is a biguanide (preferably metformin hydrochloride), the median size of the biguanide (preferably metformin hydrochloride) is preferably 10 to 100 μm, more preferably 10 to 80 μm.

The above-mentioned preferable median size is applied to an active ingredient (except insulin sensitizers) used as a starting material (including a pulverized product obtained by pulverizing, a mixed pulverized product obtained by pulverizing together with an excipient, and the like, during the production process of a solid preparation) for producing the solid preparation of the present invention. In other words, the median size of an active ingredient may have changed due to the coagulation of the active ingredient and the like, during the production process of the solid preparation of the present invention, or during the process of preserving the solid preparation after production.

As the active ingredient (except insulin sensitizers) having a desired median size mentioned above, for example, a commercially available product can be used. In addition, the active ingredient having a desired median size can also be produced by pulverization of an active ingredient having a large median size. Here, the pulverization is performed according to a known method using, for example, a cutter mill, a hammer mill, a jet mill and the like.

In particular, when a solid preparation is produced using an active ingredient having a weak binding force and a comparatively large median size, use of a large amount of additives such as a binder and the like, and the like needs to be designed to achieve sufficient preparation hardness. However, by making the median size of an active ingredient smaller, a large amount of additives such as a binder and the like becomes unnecessary, which makes it possible to increase the drug content of the solid preparation.

As for the active ingredient (except insulin sensitizers) having a desired median size mentioned above, the dispersibility thereof is preferably such that "particles of not more than 0.1 μm are contained at not more than 1% of the total amount, and particles of not less than 3000 μm are contained at not more than 10% of the total amount".

In the solid preparation of the present invention, as the active ingredient (except insulin sensitizers), one whose effective amount (or content in solid preparation) is not less than 2 parts by weight, preferably 5-700 parts by weight, more preferably 10-500 parts by weight, per 1 part by weight of an effective amount (or content in solid preparation) of an insulin sensitizer. By applying such active ingredient (except insulin sensitizers) to the solid preparation of the present invention, a particularly remarkable effect, namely, in vivo dissolution behavior of an insulin sensitizer, which is similar to the dissolution behavior of an insulin sensitizer from "a solid preparation containing the insulin sensitizer alone as an active ingredient" can be obtained.

In the solid preparation of the present invention, a particularly remarkable effect, namely, in vivo dissolution behavior of an insulin sensitizer, which is similar to the dissolution behavior of an insulin sensitizer from "a solid preparation containing the insulin sensitizer alone as an active ingredient" can be obtained when a compound having pk 4-7 is used as an insulin sensitizer and a compound having pk 10-13 is used as an active ingredient (except insulin sensitizers).

As used herein, as an insulin sensitizer having pk 4-7, for example, pioglitazone hydrochloride, rosiglitazone maleate and the like can be mentioned. As an active ingredient (except insulin sensitizers) having pk 10-13, for example, metformin hydrochloride and the like can be mentioned.

In the solid preparation of the present invention, in vivo release of the active ingredient (except insulin sensitizers) is delayed, and therefore, the influence of the active ingredient (except insulin sensitizers) on the in vivo dissolution behavior of an insulin sensitizer can be reduced.

The content of the active ingredient (except insulin sensitizers) in the solid preparation of the present invention is, for example, 0.01-100 parts by weight, preferably 1-99 parts by weight, per 100 parts by weight of the solid preparation.

Particularly, when the active ingredient (except insulin sensitizers) is biguanide (preferably metformin hydrochloride), the content of biguanide (preferably metformin hydrochloride) in the solid preparation of the present invention is preferably 5-98 parts by weight, more preferably 15-96 parts by weight, per 100 parts by weight of the solid preparation.

The most preferable combination of an insulin sensitizer and an active ingredient (except insulin sensitizers) in the solid preparation of the present invention is that of pioglitazone hydrochloride and metformin hydrochloride.

As the "microcrystalline cellulose having a mean particle size of 5-25 μm" and "microcrystalline cellulose having a mean particle size of 30-100 μm" to be used in the present invention, commercially available products can be respectively used.

In the present description, the mean particle size means one based on the weight distribution, which is preferably the same as the aforementioned median size.

As the "microcrystalline cellulose having a mean particle size of 5-25 μm", for example, Avicel PH F20 (trade name, ASAHI KASEI CHEMICALS CORPORATION), Avicel PH-M06 (trade name, ASAHI KASEI CHEMICALS CORPORATION), Avicel PH-M15 (trade name, ASAHI KASEI CHEMICALS CORPORATION), Avicel PH-M25 (trade name, ASAHI KASEI CHEMICALS CORPORATION) and the like can be used.

The content of the "microcrystalline cellulose having a mean particle size of 5-25 μm" in the solid preparation of the present invention is, for example, 0.1-50 parts by weight, preferably 0.5-40 parts by weight, per 100 parts by weight of the solid preparation.

As the "microcrystalline cellulose having a mean particle size of 30-100 μm", for example, Avicel PH 101 (trade name, ASAHI KASEI CHEMICALS CORPORATION), Avicel PH 102 (trade name, ASAHI KASEI CHEMICALS CORPORATION), Avicel PH301 (trade name, ASAHI KASEI CHEMICALS CORPORATION), Avicel PH302 (trade name, ASAHI KASEI CHEMICALS CORPORATION), Ceolus KG-802 (trade name, ASAHI KASEI CHEMICALS CORPORATION) and the like can be used.

The content of the "microcrystalline cellulose having a mean particle size of 30-100 μm" in the solid preparation of the present invention is, for example, 0.1-50 parts by weight, preferably 0.5-40 parts by weight, per 100 parts by weight of the solid preparation.

The above-mentioned mean particle size is applied to microcrystalline cellulose to be used as a starting material for the production of the solid preparation of the present invention. That is, the above-mentioned mean particle size may change during the production process of the solid preparation of the present invention, or during the process of preserving the solid preparation after production.

In the solid preparation of the present invention, by changing the mixing ratio of the "microcrystalline cellulose having a mean particle size of 5-25 μm" and the "microcrystalline cellulose having a mean particle size of 30-100 μm", in vivo dissolution behavior of the insulin sensitizer and/or active ingredient (except insulin sensitizers) from the solid preparation can be controlled.

In the solid preparation of the present invention, 1-10 parts by weight of the "microcrystalline cellulose having a mean particle size of 5-25 μm" is preferably used per 1 part by weight of the "microcrystalline cellulose having a mean particle size of 30-100 μm".

As the "polyvinylpyrrolidone K-90" to be used in the present invention, a commercially available product can be used. The "polyvinylpyrrolidone K-90" may be referred to as "povidone K-90" or "polyvidone K-90". The content of the "polyvinylpyrrolidone K-90" in the solid preparation of the. present invention is, for example, 0.1-20 parts by weight, preferably 0.5-15 parts by weight, per 100 parts by weight of the solid preparation.

As the dosage form of the solid preparation of the present invention, for example, tablet, capsule, troche and the like can be mentioned. Of these, tablet (preferably multiplelayer tablet) is preferable. Furthermore, the shape of the solid preparation may be any such as round, caplet, oblong and the like. When the weight of the solid preparation is large, the shapes of caplet and oblong are preferable from the aspect of easy swallowability.

The solid preparation of the present invention may contain an additive conventionally used for the technical field of pharmaceutical preparations. As such additive, for example, excipient, disintegrant, binder, lubricant, coloring agent, pH adjusting agent, surfactant, stabilizer, acidulant, flavor, glidant and the like can be mentioned. These additives are used in the amounts conventionally employed in the technical field of pharmaceutical preparations.

As the excipient, for example, starches such as cornstarch, potato starch, wheat starch, rice starch, partly pregelatinized starch, pregelatinized starch, porous starch and the like; sugars and sugar alcohols such as lactose, fructose, glucose, mannitol, sorbitol and the like; anhydrous calcium phosphate, crystalline cellulose, precipitated calcium carbonate, calcium silicate and the like can be mentioned.

As the disintegrant, for example, carboxymethyl cellulose (carmellose), calcium carboxymethyl cellulose (carmellose calcium), sodium carboxymethyl starch, croscarmellose sodium, crospovidone, low-substituted hydroxypropyl cellulose, hydroxypropyl starch and the like are used. The amount of the disintegrant to be used is preferably 0.5-25 parts by weight, more preferably 1-15 parts by weight, per 100 parts by weight of the solid preparation of the present invention.

As the binder, for example, hydroxypropyl cellulose, hydroxypropylmethyl cellulose, polyvinylpyrrolidone, gum arabic powder and the like can be mentioned. The amount of the binder to be used is preferably 0.1-50 parts by weight, more preferably 0.5-40 parts by weight, per 100 parts by weight of the solid preparation of the present invention. The binder is preferably hydroxypropyl cellulose or polyvinylpyrrolidone.

Preferable examples of the lubricant include magnesium stearate, calcium stearate, talc, sucrose esters of fatty acids, sodium stearyl fumarate and the like.

As the coloring agent, for example, food colors such as Food Yellow No. 5 (Sunset Yellow, the same as yellow food color NO. 6 in the US), Food Red No. 2, Food Blue No. 2 and the like, food lake colors, diiron trioxide and the like can be mentioned.

As the pH adjusting agent, citrate, phosphate, carbonate, tartrate, fumarate, acetate, amino acid salt and the like can be mentioned.

As the surfactant, sodium lauryl sulfate, polysorbate 80, polyoxyethylene (160) polyoxypropylene (30) glycol and the like can be mentioned.

As the stabilizer, for example, tocopherol, tetrasodium edetate, nicotinamide, cyclodextrins and the like can be mentioned.

As the acidulant, for example, ascorbic acid, citric acid, tartaric acid, malic acid and the like can be mentioned.

As the flavor, for example, menthol, peppermint oil, lemon oil, vanillin and the like can be mentioned.

As the glidant, for example, light anhydrous silicic acid, silicon dioxide hydrate and the like can be mentioned. As used herein, light anhydrous silicic acid may be any as long as it contains silicon dioxide hydrate ($SiO_2 \cdot nH_2O$) (n is an integer) as the main component, and as concrete examples thereof, Sylysia320 (trade name, Fuji Silysia Chemical Ltd.), AEROSIL200 (trade name, NIPPON AEROSIL CO., LTD.) and the like can be mentioned.

The above-mentioned additives may be used in a mixture of two or more kinds thereof at an appropriate ratio.

The solid preparation of the present invention can be produced, for example, according to the following production steps.

An insulin sensitizer is mixed with the aforementioned additives where necessary, and compression-shaped where necessary to give a "layer containing an insulin sensitizers".

In addition, (a) an active ingredient (except insulin sensitizers), (b) microcrystalline cellulose having a mean particle size of 5-25 μm, (c) microcrystalline cellulose having a mean particle size of 30-100 μm and (d) polyvinylpyrrolidone K-90 are mixed with the aforementioned additives where necessary, and compression-shaped where necessary to give a "layer containing the aforementioned components (a)-(d)".

The "layer containing an insulin sensitizer" obtained as mentioned above is compression-shaped around the "layer containing the aforementioned components (a)-(d)" or the "layer containing an insulin sensitizer" is superimposed on the "layer containing the aforementioned components (a)-(d)" in layers, and compression-shaped (preferably tableted) to give formed products (e.g., nucleated tablet and multiplelayer tablet, preferably multiplelayer tablet). It is possible to form an intermediate layer using inactive additives (e.g., excipient) to avoid direct contact of each layer.

The thus-obtained formed products are filled in a capsule (e.g., gelatin capsule) to give a capsule. The capsule is also encompassed in the solid preparation of the present invention.

Moreover, a coated preparation can be produced by coating the formed product mentioned above with a coating base. The coated preparation is also encompassed in the solid preparation of the present invention.

As the coating base here, for example, a sugar coating base, a water-soluble film coating base, an enteric film coating base, a sustained-release film coating base and the like can be mentioned.

As the sugar coating base, sucrose is used, and one or more kinds selected from talc, precipitated calcium carbonate, gelatin, gum arabic, pullulan, carnauba wax and the like may be further used in combination.

As the water-soluble film coating base, for example, cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; polysaccharides such as pullulan etc.; and the like can be mentioned.

As the enteric film coating base, for example, cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; naturally occurring substances such as shellac etc.; and the like can be mentioned.

As the sustained-release film coating base, for example, cellulose polymers such as ethyl cellulose etc.; acrylic polymers such as aminoalkyl methacrylate copolymer RS [Eudragit RS (trade name)], ethyl acrylate-methyl methacrylate copolymer suspension [Eudragit NE (trade name)] etc.; and the like can be mentioned.

The aforementioned coating bases may be used after mixing with two or more kinds thereof at appropriately ratios. For coating, coating additives may be used.

As the coating additive, for example, light shielding agents and/or coloring agents such as titanium oxide, talc, diiron trioxide and the like; plasticizers such as polyethylene glycol, triethyl citrate, castor oil, polysorbates and the like; organic acids such as citric acid, tartaric acid, malic acid, ascorbic acid and the like; and the like can be mentioned.

When a coated preparation is produced by coating the above-mentioned shaped product, the proportion of the shaped product is generally 70-99 parts by weight, preferably 90-98 parts by weight, per 100 parts by weight of the coated preparation.

In addition, a mark or a letter may be printed on the solid preparation of the present invention for identifiability, and a separating line may be made to facilitate division.

From the aspects of easy swallowability, preparation strength and the like, the solid preparation of the present invention is preferably film coated.

In the aforementioned production step, operation of mixing, compression-shaping, coating and the like is performed according to conventional methods in the technical field of pharmaceutical preparations.

For example, mixing is performed using a mixer such as V-TYPE MIXER, tumbler mixer and the like, and a granulator such as high speed mixer granulator, fluidized bed granulator-dryer and the like; compression-shaping is performed using a single punch tableting machine, a rotary tableting machine and the like; and coating is performed using a film coating apparatus and the like.

For compression-shaping using a single punch tableting machine, a rotary tableting machine and the like, a tableting pressure of generally 1-35 kN/cm$^2$ (preferably 5-35 kN/cm$^2$) is preferably used. Furthermore, a tapered die is preferably used for preventing capping.

The solid preparation of the present invention can be administered orally or parenterally and safely to mammals (e.g., mouse, rat, rabbit, cat, dog, bovine, horse, monkey, human and the like).

The solid preparation of the present invention and each component (e.g., insulin sensitizer such as pioglitazone hydrochloride and the like) in the solid preparation are useful as an agent for the prophylaxis or treatment of, for example, diabetes (e.g., type-1 diabetes, type-2 diabetes, gestational diabetes), hyperlipidemia (e.g., hypertriglyceridemia, hypercholesterolemia, hypo-HDL-emia, postprandial hyperlipidemia), impaired glucose tolerance [IGT (Impaired Glucose Tolerance)], diabetic complications [e.g., neuropathy, nephropathy, retinopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], obesity, osteoporosis, cachexia (e.g., cancerous cachexia, tuberculous cachexia, diabetic cachexia, blood disease cachexia, endocrine disease cachexia, infectious disease cachexia or cachexia due to acquired immunodeficiency syndrome), fatty liver, hypertension, polycystic ovary syndrome, kidney disease (e.g., diabetic nephropathy, glomerular nephritis, glomerulosclerosis, nephrotic syndrome, hypertensive nephrosclerosis, end stage kidney disease), muscular dystrophy, myocardial infarction, angina pectoris, cerebrovascular accident (e.g., cerebral infarction, cerebral apoplexy), insulin resistance syndrome, Syndrome X, Dysmetabolic syndrome, hyperinsulinemia, hyperinsulinemia-induced sensory disorder, tumor (e.g., leukemia, breast cancer, prostate cancer, skin cancer), irritable bowel syndrome, acute or chronic diarrhea, inflammatory diseases [e.g., Alzheimer's disease, chronic rheumatoid arthritis, spondylitis deformans, osteoarthritis, lumbago, gout, postoperative or traumatic inflammation, swelling, neuralgia, pharyngolaryngitis, cystitis, hepatitis (inclusive of nonalcoholic steatohepatitis), pneumonia, pancreatitis, inflammatory bowel disease, ulcerative colitis], visceral obesity syndrome, arteriosclerosis (e.g., atherosclerosis) and the like.

The solid preparation of the present invention and each component (e.g., insulin sensitizer such as pioglitazone hydrochloride and the like) in the solid preparation are useful for the secondary prevention of various diseases mentioned above (e.g., secondary prevention of cardiovascular event such as myocardial infarction etc.) and suppression of progression (e.g., suppression of progression of impaired glucose tolerance into diabetes, suppression of progression of arteriosclerosis in diabetic patients).

The dose of the solid preparation of the present invention only needs to be an effective amount of an insulin sensitizer and an active ingredient (except insulin sensitizers) contained in the solid preparation.

The effective amount of the insulin sensitizer is, for example, generally 0.01-500 mg/day, preferably 0.1-100 mg/day, for an adult (body weight 60 kg).

Particularly, when the insulin sensitizer is pioglitazone hydrochloride, the effective amount of pioglitazone hydrochloride is generally 7.5-60 mg/day, preferably 15-60 mg/day, as pioglitazone for an adult (body weight 60 kg).

When the insulin sensitizer is rosiglitazone malate, the effective amount of rosiglitazone malate is generally 1-12 mg/day, preferably 2-8 mg/day, for an adult (body weight 60 kg)

The effective amount of the active ingredient (except insulin sensitizers) is, for example, generally 0.01-10000 mg/day, preferably 0.1-5000 mg/day, for an adult (body weight 60 kg).

Particularly, when the active ingredient is a biguanide (preferably metformin hydrochloride), the effective amount of a biguanide (preferably metformin hydrochloride) is generally 125-2550 mg/day, preferably 250-2550 mg/day, for an adult (body weight 60 kg).

The frequency of the administration of the solid preparation of the present invention to the aforementioned mammals per day is preferably 1 or 2 times a day, more preferably once a day. Particularly, the solid preparation of the present invention is preferably administered once to a mammal before breakfast.

Particularly preferable examples of the solid preparation of the present invention include "a tablet (preferably multiplelayer tablet) containing 16.53 mg of pioglitazone hydrochloride (15 mg as pioglitazone) and 850 mg of metformin hydrochloride per tablet";

"a tablet (preferably multiplelayer tablet) containing 16.53 mg of pioglitazone hydrochloride (15 mg as pioglitazone) and 500 mg of metformin hydrochloride per tablet";

"a tablet (preferably multiplelayer tablet) containing 16.53 mg of pioglitazone hydrochloride (15 mg as pioglitazone) and 1000 mg of metformin hydrochloride per tablet".

The solid preparation of the present invention may be used in combination with one or more pharmaceutical agents selected from therapeutic agents for diabetes, therapeutic agents for diabetic complications, therapeutic agents for hyperlipidemia, antihypertensive agents, antiobesity agents, diuretics, antithrombotic agents and the like (hereinafter sometimes to be abbreviated as a concomitant drug). As such concomitant drugs, those exemplified above as the active ingredient can be used. The timing of administration of the solid preparation of the present invention and that of the concomitant drug are not limited, and they may be administered simultaneously or in a staggered manner to the administration subject. In addition, the solid preparation of the present invention and the concomitant drug may be administered to an administration subject as a single preparation containing them.

The dose of the concomitant drug can be appropriately selected based on the dose employed clinically. In addition, the mixing ratio of the solid preparation of the present invention and the concomitant drug can be appropriately selected according to the administration subject, administration route, target disease, condition, combination, and the like. For example, when the administration subject is a human, the concomitant drug may be used in an amount of 0.01 to 100 parts by weight per 1 part by weight of the solid preparation of the present invention.

Use of the concomitant drug in this way provides superior effects such as 1) enhancing the action of the solid preparation of the present invention or the concomitant drug (synergistic effect on the action of drugs), 2) reducing the dose of the solid preparation of the present invention or the concomitant drug (effect of reducing the dose of drugs as compared to a single drug administration), 3) reducing the secondary action of the solid preparation of the present invention or the concomitant drug, and the like.

The present invention further provides "a solid preparation containing a compound having pk 4-7 and a compound having pk 10-13, wherein in vivo release of the compound having pk 10-13 is delayed" (hereinafter sometimes to be abbreviated as the preparation of the present invention).

The preparation of the present invention provides such a superior effect, by delaying in vivo release of the compound having pk 10-13 as compared to that of the compound having pk 4-7, that the in vivo dissolution behavior of the compound having pk 4-7 and the compound having pk 10-13 is closely similar to the in vivo dissolution behavior of each compound from two kinds of solid preparations containing these compounds independently.

Here, as the compound having pk 4-7, for example, pioglitazone hydrochloride, rosiglitazone maleate, glimepiride, glipizide, glibenclamide and the like can be mentioned. Of these, pioglitazone hydrochloride is preferable. As the compound having pk 10-13, for example, metformin, a salt thereof (preferably metformin hydrochloride) and the like can be mentioned.

For example, when a compound having pk 10-13 (preferably metformin hydrochloride) has a property to change (preferably delay) the in vivo dissolution behavior of a compound having pk 4-7 (preferably pioglitazone hydrochloride), the influence (specifically, delay of in vivo dissolution) of the compound having pk 10-13 on the in vivo dissolution behavior of a compound having pk 4-7 can be reduced by applying the preparation of the present invention to these compounds.

The content of the compound having pk 4-7 in the preparation of the present invention is, for example, 0.01-100 parts by weight, preferably 1-99 parts by weight, per 100 parts by weight of the preparation.

Particularly, when the compound having pk 4-7 is pioglitazone hydrochloride, the content of pioglitazone hydrochloride in the preparation of the present invention is preferably 0.01-15 parts by weight, more preferably 0.5-10 parts by weight, per 100 parts by weight of the preparation.

The content of the compound having pk 10-13 in the preparation of the present invention is, for example, 0.01-100 parts by weight, preferably 1-99 parts by weight, per 100 parts by weight of the preparation.

Particularly, when the compound having pk 10-13 is metformin or a salt thereof (preferably metformin hydrochloride), the content of metformin or a salt thereof (preferably metformin hydrochloride) in the preparation of the present invention is, for example, preferably 5-98 parts by weight, more preferably 15-96 parts by weight, per 100 parts by weight of the preparation.

In the preparation of the present invention, the compound having pk 10-13 is used in a proportion of not less than 2 parts by weight, preferably 5-700 parts by weight, more preferably 10-500 parts by weight, per 1 part by weight of the compound having pk 4-7.

As the dosage form and shape of the preparation of the present invention, those mentioned above for the solid preparation of the present invention can be mentioned. In addition, the preparation of the present invention may contain additives conventionally used in the technical field of pharmaceutical preparations, as in the case of the solid preparation of the present invention mentioned above.

Specific examples of the preparation of the present invention include the aforementioned solid preparation of the present invention, wherein the insulin sensitizer is a compound having pk 4-7 and the active ingredient (except insulin sensitizers) is a compound having pk 10-13.

The preparation of the present invention is used for mammals (e.g., mouse, rat, rabbit, cat, dog, bovine, horse, swine, human and the like) as an agent for the prophylaxis or treatment of a target disease for which a compound having pk 4-7 and/or a compound having pk 10-13 are/is effective.

The dose of the preparation of the present invention only needs to be an effective amount of a compound having pk 4-7 and a compound having pk 10-13.

The present invention further provides "a solid preparation containing (1) metformin or a salt thereof, (2) microcrystalline cellulose having a mean particle size of 5-25 μm and (3) microcrystalline cellulose having a mean particle size of 30-100 μm, wherein the release of the metformin or a salt thereof is controlled" (hereinafter sometimes to be abbreviated as a release control preparation of the present invention).

As used herein, as the salt of metformin, for example, hydrochloride, fumarate, succinate and the like can be mentioned. Of these, hydrochloride is preferable.

The content of metformin or a salt thereof in the release control preparation of the present invention is preferably 5-98 parts by weight, more preferably 15-96 parts by weight, per 100 parts by weight of the solid preparation.

As the "microcrystalline cellulose having a mean particle size of 5-25 μm" and the "microcrystalline cellulose having a mean particle size of 30-100 μm", those used for the aforementioned solid preparation of the present invention can be mentioned. The contents of these microcrystalline celluloses in the release control preparation of the present invention are the same as those in the aforementioned solid preparation of the present invention.

In the release control preparation of the present invention, the release of metformin or a salt thereof from the solid preparation can be controlled by changing the mixing ratio of the "microcrystalline cellulose having a mean particle size of 5-25 μm" and the "microcrystalline cellulose having a mean particle size of 30-100 μm". Specifically, the release of metformin or a salt thereof from the solid preparation can be delayed by increasing the amount of the "microcrystalline cellulose having a mean particle size of 5-25 μm" and the release of metformin or a salt thereof from the solid preparation can be accelerated by increasing the amount of the "microcrystalline cellulose having a mean particle size of 30-100 μm".

As the dosage form and shape of the release control preparation of the present invention, those mentioned above for the solid preparation of the present invention can be mentioned. In addition, the release control preparation of the present invention may contain additives conventionally used in the technical field of pharmaceutical preparations, as in the case of the solid preparation of the present invention mentioned above.

The release control preparation of the present invention can be used for mammals (e.g., mouse, rat, rabbit, cat, dog, bovine, horse, swine, human) as an agent for the prophylaxis or treatment of various diseases, as in the case of the aforementioned solid preparation of the present invention.

The dose of the release control preparation of the present invention only needs to be an effective amount of metformin or a salt thereof (preferably 250-2550 mg/day).

In the release control preparation of the present invention, the release of metformin or a salt thereof from the solid preparation can be controlled (preferably delayed) by the use of two kinds of microcrystalline cellulose having different mean particle sizes.

According to the release control preparation of the present invention, adverse influence (e.g., uncomfortable feeling in the stomach, vomiting, diarrhea) caused by metformin or a salt thereof in the body can be reduced by controlling (preferably delaying) the release of metformin or a salt thereof from the solid preparation.

Moreover, since the release control preparation of the present invention does not require use of a large amount of a binder (specifically polyvinylpyrrolidone) as compared to commercially available preparations (e.g., GLUCOPHAGE, trade name) containing metformin hydrochloride, it is superior in the productivity of preparation, uniform drug content, drug releasability and the like.

The release control preparation of the present invention may be used in combination with a concomitant drug exemplified for the aforementioned solid preparation of the present invention. The concomitant drug is preferably an insulin sensitizer, more preferably pioglitazone hydrochloride.

When the release control preparation of the present invention is used in combination with the above-mentioned concomitant drug, since release of metformin or a salt thereof from the release control preparation is delayed, an adverse influence (e.g., decomposition of drug, degraded activity of drug, variation in the dissolution pattern of drug) of metformin or a salt thereof on the concomitant drug can be suppressed.

EXAMPLES

The present invention is explained in detail in the following by referring to Reference Examples, Examples, and Experimental Example, which are not to be construed as limitative.

In the following Reference Examples and Examples, as various additives such as magnesium stearate and the like, the Japanese Pharmacopoeia 14th Edition compatible products or Japanese Pharmaceutical Excipients 2003 compatible products were used.

Reference Example 1

Metformin hydrochloride (median size: 29 μm, 10200 g), and Avicel PH F20 (trade name)-(396 g) were placed in a fluidized bed granulator-dryer (manufactured by POWREX CORPORATION, WSG-15), granulated while spraying a solution (2516 g) of polyvinylpyrrolidone K-90 (204 g) in purified water and dried to give granules A.

The obtained granules A (9000 g) were mixed with Avicel PH F20 (trade name, 480 g), Avicel PH101 (trade name, 690 g) and magnesium stearate (30 g) to give a powder mixture A.

Reference Example 2

Pioglitazone hydrochloride (median size: 13 μm, 909.15 g), carmellose calcium (330 g) and lactose (9111.85 g) were placed in a fluidized bed granulator-dryer (manufactured by POWREX CORPORATION, WSG-15), granulated while spraying a solution (4308 g) of hydroxypropylcellulose (275 g) in purified water and dried to give granules B.

The obtained granules B (8694 g) were mixed with carmellose calcium (270 g) and magnesium stearate (36 g) to give a powder mixture B.

Reference Example 3

Pioglitazone hydrochloride (median size: 13 μm, 826.5 g), carmellose calcium (350 g) and lactose (9786 g) were placed in a fluidized bed granulator-dryer (manufactured by POWREX CORPORATION, WSG-15), granulated while spraying a solution (4545 g) of hydroxypropylcellulose (290 g) in purified water and dried to give granules D.

The obtained granules D (10127 g) were mixed with carmellose calcium (315 g) and magnesium stearate (42.75 g) to give a powder mixture D.

Reference Example 4

Pioglitazone hydrochloride (median size: 13 μm) (10000 g) and microcrystalline cellulose (2500 g, Avicel PH101 (trade name)) were placed in a mixer (POWREX CORPORATION, vertical granulator) and mixed by stirring. The obtained mixture was pulverized in a jet mill pulverizer (NPK Co., Ltd., 100SP) to give a pulverized product (median size 3.6 μm) of a pioglitazone hydrochloride/microcrystalline cellulose mixture.

Metformin hydrochloride (median size: 29 μm, 4000 g), a pulverized product (median size 3.6 μm, 82.64 g) of a pioglitazone hydrochloride/microcrystalline cellulose mixture and microcrystalline cellulose (120 g, Avicel PH101 (trade name)) were placed in a fluidized bed granulator-dryer (POWREX CORPORATION, FD-5S), granulated while spraying purified water (1300 g) containing polyvinylpyrrolidone K-30 (260 g), and dried to give granules.

The obtained granules were mixed with microcrystalline cellulose (Avicel PH101 (trade name, 341.36 g), croscarmellose sodium (240 g) and magnesium stearate (16 g).

The obtained powder mixture was tableted using a tableting machine (Kikusui Seisakusho, Ltd., Correct 12HUK, tablet size: major axis 18.5 mm×minor axis 10 mm, compression pressure: 23 kN/punch) to give tablets (weight per tablet: 1265 mg) containing metformin hydrochloride 1000 mg/pioglitazone hydrochloride 16.53 mg (15 mg as pioglitazone) per tablet.

The obtained tablets (3795 g) were charged in a film coating apparatus (DRIACOATER500, manufactured by POWREX CORPORATION) and a coating solution was sprayed at an inlet temperature of 85° C. at 15 g/min to give film-coated tablets weighing 1300 mg per tablet. As the coating solution, a dispersion (1000 g) of hydroxypropylmethyl cellulose (66.48 g), polyethylene glycol 6000 (12.84 g), titanium oxide (12.84 g) and talc (12.84 g) in purified water was used.

Example 1

The powder mixture A obtained in Reference Example 1 was tableted using a tableting machine (Kikusui Seisakusho, Ltd., AQUARIUS 0824, tablet size: major axis 18.5 mm×minor axis 10 mm, compression pressure: 3 kN/punch) to give tablets (weight per tablet: 1020 mg). Then, the powder mixture B obtained in Reference Example 2 was charged in said tableting machine and tableted (compression pressure: 25 kN/punch) to give bilayer tablets (weight per tablet: 1220 mg) containing metformin hydrochloride 850 mg/pioglitazone hydrochloride 16.53 mg (15 mg as pioglitazone) per tablet.

The obtained bilayer tablets (5600 g) were charged in a film coating apparatus (DRIACOATER500, manufactured by POWREX CORPORATION) and a coating solution was sprayed at an inlet temperature of 85° C. at 15 g/min to give film-coated tablets weighing 1255 mg per tablet. As the coating solution, a dispersion (1446 g) of hydroxypropylmethyl cellulose (101.7 g), polyethylene glycol 6000 (19.65 g), titanium oxide (19.65 g) and talc (19.65 g) in purified water was used.

Example 2

The granules A (5294 g) obtained in Reference Example 1 were mixed with Avicel PH F20 (trade name, 548 g), Avicel PH101 (trade name, 140 g) and magnesium stearate (18 g) to give a powder mixture C.

The obtained powder mixture C was tableted using a tableting machine (Kikusui Seisakusho, Ltd., AQUARIUS 0824, tablet size: major axis 16 mm×minor axis 9 mm, compression pressure: 2 kN/punch) to give tablets (weight per tablet: 600 mg). Then, the powder mixture B obtained in Reference Example 2 was charged in said tableting machine and tableted (compression pressure: 18 kN/punch) to give bilayer tablets (weight per tablet: 800 mg) containing metformin hydrochloride 500 mg/pioglitazone hydrochloride 16.53 mg (15 mg as pioglitazone) per tablet.

The obtained bilayer tablets (3900 g) were charged in a film coating apparatus (DRIACOATER500, manufactured by POWREX CORPORATION) and a coating solution was sprayed at an inlet temperature of 85° C. at 15 g/min to give film-coated tablets weighing 823 mg per tablet. As the coating solution, a dispersion (1009 g) of hydroxypropylmethyl cellulose (71.03 g), polyethylene glycol 6000 (13.70 g), titanium oxide (13.70 g) and talc (13.70 g) in purified water was used.

Example 3

The granules A (10590 g) obtained in Reference Example 1 were mixed with Avicel PH F20 (trade name, 759 g), Avicel PH101 (trade name, 618 g) and magnesium stearate (35 g) to give a powder mixture.

The obtained powder mixture was tableted using a tableting machine (Kikusui Seisakusho, Ltd., AQUARIUS 0824, tablet size: major axis 18.5 mm×minor axis 10 mm, compression pressure: 3 kN/punch) to give tablets (weight per tablet: 1200 mg). Then, the powder mixture D obtained in Reference Example 3 was charged in said tableting machine and tableted (compression pressure: 25 kN/punch) to give bilayer tablets (weight per tablet: 1433 mg) containing metformin hydrochloride 1000 mg/pioglitazone hydrochloride 16.53 mg (15 mg as pioglitazone) per tablet.

The obtained bilayer tablets (5445 g) were charged in a film coating apparatus (DRIACOATER500, manufactured by POWREX CORPORATION) and a coating solution was sprayed at an inlet temperature of 85° C. at 15 g/min to give film-coated tablets weighing 1475 mg per tablet. As the coating solution, a dispersion (1439 g) of hydroxypropylmethylcellulose (101.1 g), polyethylene glycol 6000 (19.53 g), titanium oxide (19.53 g) and talc (19.53 g) in purified water was used.

Experimental Example

The tablets obtained in the aforementioned Examples were evaluated for the dissolution property of pioglitazone hydrochloride by the Paddle Method (50 rpm) using a hydrochloric acid-potassium chloride buffer (900 mL, 37° C., pH 2.0). The results are shown in Table 1.

TABLE 1

| | Dissolution rate (%) of pioglitazone hydrochloride | | | |
|---|---|---|---|---|
| | time | | | |
| | 15 min | 30 min | 45 min | 60 min |
| Example 1 | 93.9 | 101.1 | 101.8 | 101.8 |
| Example 2 | 94.3 | 98.5 | 99.6 | 100.0 |

As shown in Table 1, the solid preparation of the present invention showed superior dissolution property of pioglitazone hydrochloride.

Industrially Applicability

The solid preparation of the present invention is useful as a therapeutic drug for diabetes and the like and has bioequivalence to two kinds of solid preparations independently containing an insulin sensitizer and an active ingredient (except insulin sensitizers).

Particularly, the solid preparation of the present invention shows in vivo dissolution behavior of an insulin sensitizer, which is similar to the dissolution behavior of an insulin sensitizer from "a solid preparation containing an insulin sensitizer alone as an active ingredient".

While some of specific embodiments of the present invention have been described in detail in the above, it will, however, be evident for those of ordinary skill in the art that various modifications and changes may be made to the particular embodiments shown without substantially departing from the novel teaching and advantages of the present invention. Such modifications and changes are encompassed in the spirit and scope of the present invention as set forth in the appended claims.

This application is based on a patent application No. 2004-118907 filed in Japan on Apr. 14, 2004, the contents of which are incorporated in full herein by this reference.

The invention claimed is:

1. A multiple-layer tablet comprising (1) a layer containing pioglitazone hydrochloride having a median size of 1 to 50 μm and (2) a layer containing (a) metformin hydrochloride having a median size of 10 to 100 μm, (b) microcrystalline cellulose having a mean particle size of 5-25 μm, (c) microcrystalline cellulose having a mean particle size of 30-100 μm and (d) polyvinylpyrrolidone K-90 in an amount of 0.1-20 parts by weight per 100 parts by weight of the multiple-layer tablet, wherein the release of metformin hydrochloride is delayed compared to release of pioglitazone hydrochloride.

2. A production method of the multiple-layer tablet of claim 1, which comprises stacking (1) a layer containing pioglitazone hydrochloride having a median size of 1 to 50 μm, and (2) a layer containing (a) metformin hydrochloride having a median size of 10 to 100 μm, (b) microcrystalline cellulose having a mean particle size of 5-25 μm, (c) microcrystalline cellulose having a mean particle size of 30-100 μm and (d) polyvinylpyrrolidone K-90 in an amount of 0.1-20 parts by weight per 100 parts by weight of the multiple-layer tablet, in layers and tableting them, wherein the release of metformin hydrochloride is delayed compared to release of pioglitazone hydrochloride.

3. A multiple-layer tablet comprising (1) a layer containing pioglitazone hydrochloride having a median size of 1 to 50 μm and (2) a layer containing (a) metformin hydrochloride having a median size of 10 to 100 μm, (b) microcrystalline cellulose having a mean particle size of 5-25 μm, (c) microcrystalline cellulose having a mean particle size of 30-100 μm and (d) polyvinylpyrrolidone K-90 in an amount of 0.1-20 parts by weight per 100 parts by weight of the multiple-layer tablet, wherein the release of metformin hydrochloride is delayed compared to release of pioglitazone hydrochloride, and, wherein the pioglitazone hydrochloride and metformin hydrochloride show bioequivalence to administration of a first tablet comprising pioglitazone hydrochloride and a second tablet comprising metformin hydrochloride.

4. The production method of claim 2, wherein the pioglitazone hydrochloride and metformin hydrochloride show bioequivalence to administration of a first tablet comprising pioglitazone hydrochloride and a second tablet comprising metformin hydrochloride.

5. A multiple-layer tablet comprising (1) a layer containing pioglitazone hydrochloride having a median size of 1 to 50 μm and (2) a layer containing (a) metformin hydrochloride having a median size of 10 to 100 μm, (b) microcrystalline cellulose having a mean particle size of 5-25 μm, (c) microcrystalline cellulose having a mean particle size of 30-100 μm and (d) polyvinylpyrrolidone K-90 in an amount of 0.1-20 parts by weight per 100 parts by weight of the multiple-layer tablet, wherein the pioglitazone hydrochloride is at least about 98.5% dissolved in 30 minutes when the tablet is stirred in a hydrochloric acid-potassium chloride buffer.

6. The tablet of claim 1, wherein the tablet comprises about 16.53 mg of pioglitazone hydrochloride and about 850 mg of metformin hydrochloride.

7. The tablet of claim 1, wherein the tablet comprises about 16.53 mg of pioglitazone hydrochloride and about 500 mg of metformin hydrochloride.

8. The tablet of claim 1, wherein the tablet comprises about 16.53 mg of pioglitazone hydrochloride and about 1000 mg of metformin hydrochloride.

9. A multiple-layer tablet consisting of (1) a layer containing pioglitazone hydrochloride having a median size of 1 to 50 μm and (2) a layer containing (a) metformin hydrochloride having a median size of 10 to 100 μm, (b) microcrystalline cellulose having a mean particle size of 5-25 μm, (c) microcrystalline cellulose having a mean particle size of 30-100 μm and (d) polyvinylpyrrolidone K-90 in an amount of 0.1-20 parts by weight per 100 parts by weight of the multiple-layer tablet, wherein release of metformin hydrochloride is delayed compared to release of pioglitazone hydrochloride.

* * * * *